United States Patent [19]

Mittleman

[11] 4,413,990
[45] Nov. 8, 1983

[54] AIR BYPASS VALVE ASSEMBLY FOR A MEDICAL FLUID ADMINISTRATION SET

[75] Inventor: Herbert Mittleman, Deerfield, Ill.

[73] Assignee: Baxter Travenol Laboratories, Inc., Deerfield, Ill.

[21] Appl. No.: 298,234

[22] Filed: Aug. 31, 1981

[51] Int. Cl.³ .............................................. A61M 1/00
[52] U.S. Cl. .................................... 604/122; 604/129
[58] Field of Search ........... 128/214 C, 214 E, 214 F, 128/DIG. 12; 137/852, 854, 150; 222/152, 478; 604/122–126, 251–253, 256, 257, 246, 129

[56] References Cited

U.S. PATENT DOCUMENTS

| 1,048,744 | 12/1912 | Schoop | 137/150 |
| 1,846,307 | 2/1932 | Bush . | |
| 2,389,185 | 11/1945 | Dick | 210/62 |
| 2,704,544 | 3/1955 | Ryan | 604/252 |
| 2,895,613 | 7/1959 | Griffiths | 210/130 |
| 2,917,110 | 12/1959 | Brohl | 158/36 |
| 3,003,500 | 10/1961 | Barton et al. | 128/214 C |
| 3,156,645 | 11/1964 | Chapin et al. | 210/120 |
| 3,216,419 | 11/1965 | Scislowicz | 128/214 |
| 3,291,151 | 12/1966 | Loken | 128/DIG. 12 |
| 3,403,696 | 10/1968 | Pynchon | 137/852 |
| 3,423,939 | 1/1969 | Lewis et al. | 137/852 |
| 3,832,141 | 8/1974 | Haldopoulos | 23/259 |
| 3,846,077 | 11/1974 | Ohringer | 23/259 |
| 3,881,640 | 5/1975 | Noble | 128/214 C |
| 3,935,111 | 1/1976 | Bentley | 210/446 |
| 3,951,145 | 4/1976 | Smith | 128/214 R |
| 3,954,623 | 5/1976 | Hammer et al. | 604/252 |
| 3,967,620 | 7/1976 | Noiles | 128/214 C |
| 3,982,534 | 9/1976 | Buckman | 128/214 C |
| 4,056,100 | 11/1977 | Noiles | 128/214 C |
| 4,198,971 | 4/1980 | Noiles | 128/214 C |
| 4,209,485 | 6/1980 | Greenspan | 137/852 |

FOREIGN PATENT DOCUMENTS 1481427 7/1977 United Kingdom .

OTHER PUBLICATIONS

Product Information Data Sheet "Gore Tex", W. L. Gore & Assoc., Elkton, Md. 21921, Jun. 21, 1977.

Primary Examiner—C. Fred Rosenbaum
Assistant Examiner—J. L. Kruter
Attorney, Agent, or Firm—Paul C. Flattery; John P. Kirby, Jr.; Bradford R. L. Price

[57] ABSTRACT

A bypass valve assembly is provided in a medical fluid administration set to prevent rupture of a hydrophilic membrane valve of a burette in the administration set, eliminating the need for additional procedural safeguards by medical personnel during priming of the set.

8 Claims, 8 Drawing Figures

AIR BYPASS VALVE ASSEMBLY FOR A MEDICAL FLUID ADMINISTRATION SET

DESCRIPTION

TECHNICAL FIELD

The present invention relates to medical fluid administration sets, and in particular to a bypass valve assembly which relieves pressure upon a membrane valve when the drip chamber is primed.

BACKGROUND OF THE INVENTION

Administration sets for the delivery of medical fluids from a fluid source to a patient typically include a drip chamber for determining flow rate and means such as a roller clamp to control the flow rate. In an intravenous administration set the drip chamber is commonly made of a flexible plastic material. The liquid to be delivered, such as for example, dextrose solution or saline solution, enters the upstream end of the drip chamber. Drops of the liquid are formed at an orifice in the drip chamber and fall to the bottom of the drip chamber, from there proceeding downstream through the administration set into the patient. The rate at which the drops are formed are typically counted by a nurse or other medical personnel who, given the conversion factor of the number of drops per milliliter for the particular administration set, determines the volumetric flow rate of the medical fluid.

A drip chamber works by utilizing the air pressure within the drip chamber. As the liquid leaves the downstream end of the drip chamber, the volume of air remaining expands, thereby decreasing the air pressure within the drip chamber and permitting an additional drop to fall. The rate of flow out of the drip chamber is determined by a clamp or other means downstream from the drip chamber. Before the administration set is attached to the patient, the set must be primed. This is performed by squeezing and then releasing the walls of the drip chamber, drawing liquid from the solution container into the drip chamber.

A device commonly employed in-line with such an administration set is a burette for measuring specific quantities of liquid. A burette may be used when, for example, the volume to be infused into the patient is less than the volume in the supply container or when two different liquids are desired to be mixed in the burette before delivery to the patient.

In order to prevent air from entering the administration set conduit and perhaps causing an air embolism in the patient, a membrane valve is commonly placed at the bottom of the burette. Typically, this membrane valve is a hydrophilic filter which allows the liquid to pass from the burette through the filter and from there downstream through the administration set but which does not permit the passage of air from the burette. Thus, if all of the liquid in the burette passes downstream of the burette before medical personnel return to the patient's bedside, the membrane valve will prevent air in the burette from passing downstream.

Such membrane valves are usually not as structurally resistant to pressure as would be desired. A problem encountered in using such a membrane valve occurs upon priming of the administration set, discussed above. When the drip chamber downstream of the burette with membrane valve is primed, the resulting pressure from the air being forced out of the drip chamber may rupture the membrane valve.

One solution to this problem has been a procedure with the acronym O.S.C.A.R., formed from the words "Open Squeeze Close and Release". In this procedure the administration set is primed by opening the roller clamp downstream of the drip chamber (Open). Then the drip chamber itself is squeezed (Squeeze). With one hand retaining the drip chamber wall in the compressed position, the roller clamp is then closed with the other hand (Close), whereupon the drip chamber is released (Release). The drip chamber wall thereby regains its original expanded position and liquid is drawn into the drip chamber to prime the set. The roller clamp must be in the closed position during expansion of the drip chamber in order to create the necessary suction of liquid through the membrane valve. With the OSCAR procedure the increased pressure formed during drip chamber compression is relieved downstream of the membrane valve and rupture of the membrane valve is avoided.

The principal problems with this procedure are that the attending nurse may forget to use the OSCAR safeguard steps or not know that the steps are required. Also, the procedure takes additional time to perform and requires both hands. Stated differently, the OSCAR safeguard steps are time-consuming and cumbersome, not part of the usual priming technique for the majority of sets which do not have burettes, yet critical to avoid membrane valve rupture and the possibility of an air embolism which may occur if medical personnel forget to return to the patient before the burette is emptied.

One attempt to prevent membrane valve rupture while eliminating the need for OSCAR is shown is U.S. Pat. Nos. 3,967,620 and 4,056,100. The membrane valve disclosed therein is allowed to lift upwardly from its resting position to allow the passage of air around the membrane valve during compression of the drip chamber wall. This construction may be rather expensive and problems are possible with the positioning of the membrane valve itself.

FIG. 5 of the '620 patent discloses an alternate embodiment whereby a check valve is employed comprising a tubing segment having a slit therein, the tubing segment communicating between the drip chamber and the burette such that upon squeezing of the drip chamber air is forced through the slit into the burette chamber, reducing pressure on the membrane valve. Such an embodiment avoids problems with the positioning of the membrane valve but appears to be hard to manufacture consistently. In addition, it is important that upon release of the drip chamber wall that liquid or air does not pass from the burette through the check valve slit into the drip chamber. This may be difficult to avoid due to head pressure from the liquid supply which is greater than atmospheric pressure.

A further attempt to avoid membrane valve rupture is disclosed in U.S. Pat. No. 4,198,971. In the device of that disclosure an air filter 94 allows air in the drip chamber to communicate with the ambient atmosphere upon selective engagement of a rotatably mounted vent cap 82 (FIG. 5), an elastic sealing band 110 (FIG. 6) or a slide clamp 128 (FIG. 7). Selectively positioning the vent cap, sealing band or slide clamp requires an additional step in the priming procedure and appears to be an alternate means of performing OSCAR. Additionally, these selective closures may accidently be left in the open position. Indeed, the devices are meant to be operated at times in the open position to allow air to enter from the atmosphere into the drip chamber, serving as a means to lower the level of liquid in the drip chamber if same becomes flooded. Although the filter 94 is intended to remove microorganisms from the air entering the drip chamber, it does provide for communication of the atmospheric air into the set pathway. When a flexible solution container is used the need for an air vent for the solution container itself is eliminated and the only opening in the pathway is a filtered air vent in the burette. The purpose of the burette vent is not to draw in air from the atmosphere however, and a closed system is possible.

An additional problem which may be present with the device disclosed in the '971 patent is finding a filter element 94 with pore sizes small enough to function as a superior eliminator of microorganisms from the atmosphere while still allowng air to exit quickly from the drip chamber upon the compression cycle of priming to avoid rupturing the membrane valve.

The device of the present invention prevents rupture of the membrane valve, eliminates the need for the OSCAR safeguard steps and quickly and selectively permits the expulsion of air from the drip chamber, while preventing the influx into the fluid pathway of air external to the administration set during either priming or set operation, thereby maintaining what may be a closed system.

SUMMARY OF THE INVENTION

The assembly of the present invention includes an air venting bypass valve mounted in the wall of the fluid pathway in a medical solution administration set and more particularly in an administration set including a compressible drip chamber in the pathway and a membrane valve in the pathway for preventing air from passing downstream of the membrane valve in the pathway. The air venting bypass valve assembly allows priming of the drip chamber while eliminating the danger of rupture of the membrane valve, without the need for any additional step by medical personnel.

The bypass valve assembly is operable in an unstressed, first mode in which the bypass valve is closed, such that the fluid pathway is closed at the bypass valve to the ambient air outside of the administration set pathway. The bypass valve is further operable in an air-expulsing, second mode upon compression of the drip chamber, whereby the bypass valve opens due to increased pressure within the drip chamber, such that the air in the drip chamber follows the path of least resistance and exits the administration set through the bypass valve. The bypass valve shifts from the second mode to the first mode during compression of the drip chamber such that air outside the administration set does not enter the fluid pathway. In the preferred embodiment the bypass valve returns to the first mode before the air pressure in the drip chamber drops to the atmospheric air pressure, thereby preventing an influx of ambient air into the pathway.

The device of the present invention is of low-cost construction relative to other devices for preventing rupture of the membrane valve. The present invention allows for priming in the same manner as with any administration set not having a burette and the attendant membrane valve. The special OSCAR procedure is made unnecessary. Further, the bypass valve assembly of the present invention provides means for preventing membrane valve rupture while excluding outside air and contaminants from the fluid pathway.

DETAILED DESCRIPTION OF THE PREFERRED EMBODIMENT

Figure 1:
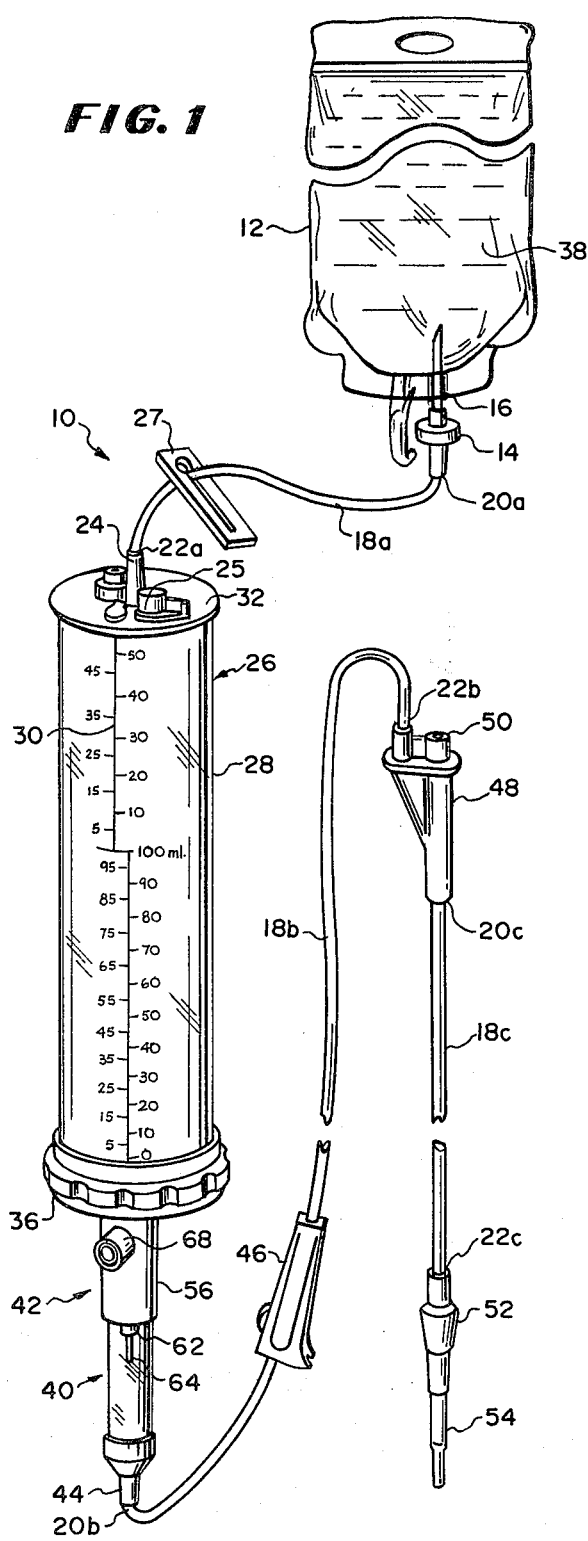
FIG. 1 is a perspective view of an intravenous administration set including the unique valve assembly construction of the present invention.
Figure 2:
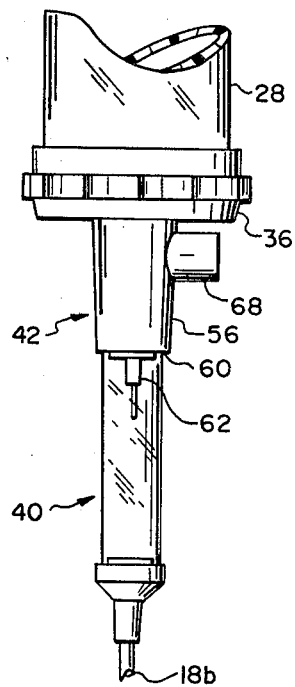
FIG. 2 is a fragmentary side elevational view of the burette chamber and drip chamber including the valve assembly.
Figure 3:
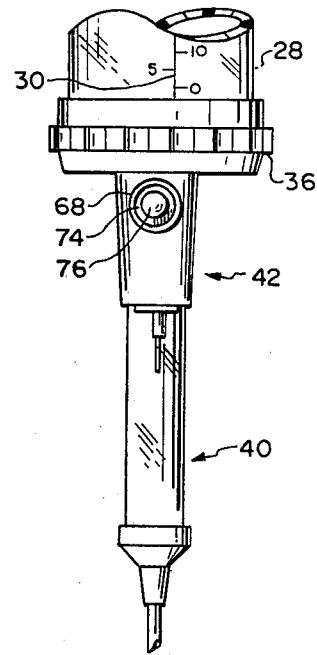
FIG. 3 is a fragmentary front elevational view taken from the right side of FIG. 2.

FIG. 1 illustrates an intravenous administration set 10 connected to a solution supply container 12 and including the assembly of the present invention. Except for the assembly of the present invention, the administration set 10 illustrated is typical of the arrangement of various elements commonly found in administration sets. The set includes a spike 14 for insertion through the port 16 of the supply container 12. Plastic tubing segment 18a is attached at its upstream end 20a to the spike 14 and at its downstream end 22a to a port 24 of a burette 26 or other chamber for measuring a specified volume of liquid. A slide clamp 27 or other means for providing selective communication of the liquid 38 in the supply container 12 with the burette 26 is mounted on the plastic tubing 18a. The burette 26 includes a transparent side wall 28 with indicia 30 for measuring the volume of liquid in the burette. The burette includes a top 32 on which the port 24 and a filtered air vent 25 are mounted. The filtered air vent 25 may be constructed so as to be selectively opened and closed.

Figure 5:
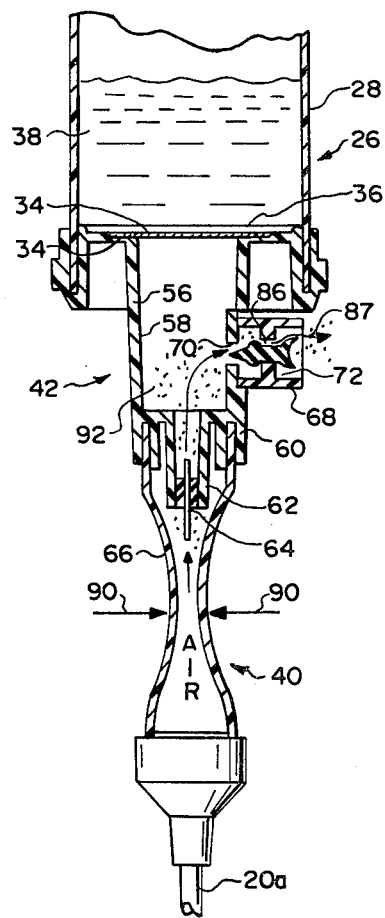
FIG. 5 is a fragmentary cross-sectional view of the assembly during compression of the drip chamber.
Figure 6:
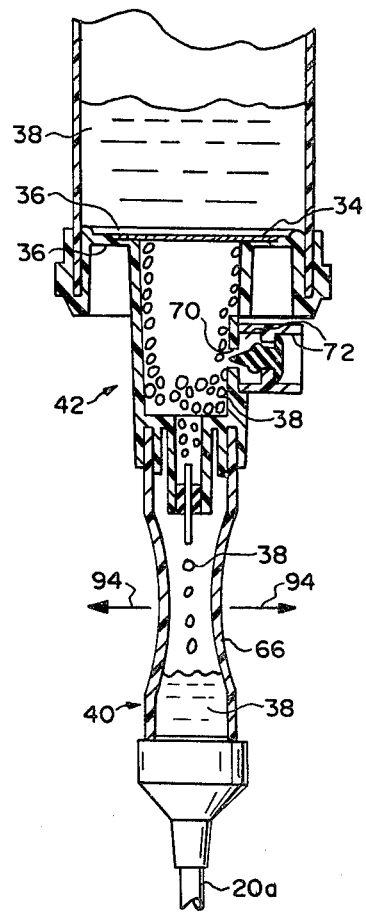
FIG. 6 is a fragmentary cross-sectional view as in FIG. 5, shown during expansion of the drip chamber.

As seen in FIGS. 5 and 6, the bottom of the burette 26 or other volume limiting chamber is defined by the membrane valve 34. The membrane valve 34 is attached to the burette 26 by membrane valve mounting 36.

Liquid 38 in the burette 26 communicates through membrane valve 34 with drip chamber 40. As seen in FIGS. 1, 2, 3, 5 and 6, the bypass valve assembly 42 of the present invention is intermediate of the membrane valve 34 and drip chamber 40. In the preferred embodiment illustrated, the bypass valve assembly 42 is made integral with and depending from the membrane valve mounting 36. Such construction is simple and has been found to be of low cost; however, as will become apparent, many other configurations of the bypass assembly are possible.

The drip chamber 40 is connected at its downstream end 44 to the upstream end 20b of a second segment of plastic tubing 18b. A roller clamp 46 for controlling the flow rate of liquid from the burette is shown on the second segment of tubing 18b.

In the administration set shown, the downstream end 22b is attched to an injection site 48 including a latex plug 50 which may be resealably pierced by a needle for the injection of additional medicament. A third segment of plastic tubing 18c is connected at its upstream end 20c to the injection site and at its downstream end 22c to a resealably pierceable rubber-like puncture indicator 52 which may be used as an injection site and which is attached to a needle adapter 54. A needle (not shown) may be attached to the needle adapter 54 for communication with, for example, the venous system of a human patient.

Turning now to the bypass valve assembly 42, a rigid plastic housing 56 is integral with and depends from the membrane valve mounting 36 of the burette 26. The housing 56 defines a housing chamber 58. At the bottom of the housing chamber 58 is a drip chamber cap 60 which may be molded integral with the housing 56. The drip chamber cap 60 includes a drop forming member 62 which may include a small metal conduit 64 which defines smaller drops in the drop forming member 62. The drip chamber wall 66 may be attached to the drip chamber cap 60 by well known means such as adhesive, heat sealing, or interference fit.

Figure 4A:
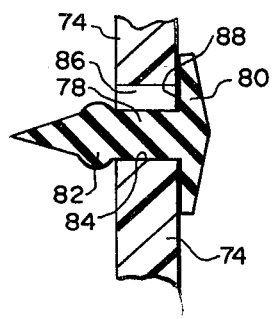
FIG. 4a is a fragmentary cross-sectional view taken through the longitudinal axis of the bypass valve and support, in the first mode.
Figure 4B:
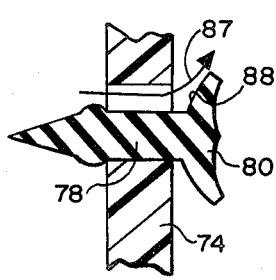
FIG. 4b is a fragmentary cross-sectional view of the valve in the second mode.
Figure 4C:
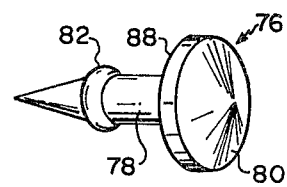
FIG. 4c is a perspective view of the valve.

Projecting from the housing 56 is a bypass valve support 68, which in the construction shown is a cylindrical projection from the housing 56. A housing opening 70 in the housing chamber 58 communicates with the atmosphere through a channel 72 defined by the bypass valve support 68. A ridge 74 projects inwardly from the valve support 68. The bypass valve 76 is mounted on the ridge 74 of the valve support 68 as seen in FIGS. 4, 5 and 6. The bypass valve 76 itself may be a known umbrella valve and includes a stem 78, cap 80 and an annular bead 82. The stem 78 fits through a ridge opening 84 in the ridge 74 and is held thereby. Adjacent to the ridge opening 84 is a groove 86 such that the ridge 74, although holding stem 78, is not adjacent to the stem about the entire circumference of the stem 78. The annular bead 82 makes difficult the inadvertent removal of the valve 76.

The bypass valve 76, or at least the cap 80 thereof, is constructed of a flexible material such as latex rubber. In the unstressed first mode as illustrated in FIG. 4a the underside 88 of the cap 80 rests against the smooth ridge 74 in sealing engagement therewith such that the groove 86 is not in open communication with the atmosphere.

In operation the bypass valve assembly 42 works as illustrated in FIGS. 4, 5 and 6. The drip chamber and thus the administration set are primed in the usual manner. As shown by arrows 90 (FIG. 5), the drip chamber wall 66 is compressed, for example, between the fingers and thumb of the hand of an operator. It is during this step that the membrane valve would be subject to dangerously high pressure were it not for the valve assembly 42. Upon compression of the drip chamber wall 66, air within the drip chamber is expulsed through the drop forming member 62 and into the housing chamber 58 of the valve assembly 42. The expulsed air 92 is illustrated graphically in FIG. 5.

The air 92 forced into the housing chamber 58 flows against the cap 80 of the bypass valve 76 through the groove 86 in the bypass valve support 68. The cap 80 is constructed so as to flex when the pressure level within the housing chamber 58 rises to a level which is less than the rupture pressure level of the membrane valve 34. Thus, the air presses against the underside 88 of the cap 80 and lifts the cap out of engagement with the ridge 74. This is the air expulsing, second mode illustrated in FIGS. 4b and 5. In the second mode the pathway-internal air 92 to be expulsed is in open communication with the atmosphere and thus exits the administration set 10, as shown by arrows 87.

It will be understood that the compression period is short in duration. However, during this time period the air pressure in the drip chamber 40 and housing chamber 58 drops from an initial high point to a level whereby the cap 80 gradually returns back to its unstressed, unflexed first mode in sealing engagement with the ridge 74. The position of the bypass valve 76 is then as shown in FIGS. 4a and 6.

After the drip chamber is squeezed, it is simply released. Because of a pressure differential, the drip chamber wall 66 expands outwardly as shown by arrows 94 (FIG. 6) to its normal operating position shown in FIGS. 1 through 3. During the expansion stage some of the liquid 38 in the burette 26 is drawn through the membrane valve 34 into the housing chamber 58 and from there into the drip chamber 40. The bypass valve 76 closes the housing chamber 58 before any air in the atmosphere with its attendant contaminants can enter the groove 86. The bypass valve 76 is designed such that it returns to its unstressed first mode, in sealing engagement with the ridge 74 and thus the administration set 10, from the air-expulsing second mode before the air pressure in the drip chamber drops to the level of the atmospheric air pressure, which thus prevents the influx of any pathway-external atmospheric air into the valve assembly 42.

Modifications of the assembly of the invention are of course possible. A drip chamber could be designed such that the bypass valve assembly is mounted directly in the side wall thereof, thereby eliminating the need for the housing chamber 58 illustrated in the drawings. The mounting for the bypass valve 76 may assume various configurations so long as it holds the bypass valve 76 while providing an opening to the atmosphere which may be selectively opened and closed by the bypass valve 76.

With the present invention, the roller clamp 46 or other tube clamping means may remain shut during the entire priming procedure. The danger of membrane valve rupture is eliminated. The present invention removes the need for a small but otherwise critical procedure in the priming operation of a medical fluid administration set having a relatively fragile membrane valve.

While one embodiment of the present invention has been described in detail and shown in the accompanying drawings, and other embodiments have also been suggested, it will be evident that various further modifications are possible without departing from the scope of the invention.

What is claimed is:

1. In a medical fluid administration set including a fluid pathway, a compressible drip chamber in the pathway and a membrane valve in the pathway preventing air from passing downstream through the membrane valve in the pathway, the improvement comprising:
air-venting bypass valve means mounted in the pathway intermediate the membrane valve and the drip chamber;
said bypass valve means operable in an unstressed, first mode wherein the pathway is closed at said bypass valve means to the atmosphere external to the pathway, and an air-expulsing, second mode upon compression of the drip chamber, wherein said bypass valve means automatically opens, permitting air in the drip chamber to exit the administration set through said bypass valve means;

said bypass valve means gradually returning to said unstressed, first mode in response to the decreasing force of the existing air, said bypass valve means relieving pressure upon the membrane valve by the air entrapped in the drip chamber during the compression thereof, said bypass valve means returning from said air-expulsing, second mode to said unstressed, first mode before the air pressure in the drip chamber drops to atmospheric pressure, thereby preventing an influx of air into the pathway through said bypass valve means.

2. A medical fluid administration set comprising:
a fluid pathway;
a compressible drip chamber in said pathway;
a membrane valve in said pathway for preventing air from passing downstream through said membrane valve in said pathway; and
air-venting bypass valve means mounted in said pathway intermediate said membrane valve and said drip chamber and operable in an unstressed, first mode wherein said pathway is closed at said bypass valve means to the atmosphere outside of said pathway, and an air-expulsing, second mode upon compression of said drip chamber, wherein said bypass valve means opens, permitting air in said drip chamber to exit said administration set through said bypass valve means;

said bypass valve means gradually returning to said unstressed, first mode in response to the decreasing force of the exiting air, said bypass valve means relieving pressure upon said membrane valve by the air entrapped in said drip chamber during the compression thereof, said bypass valve means returning from said air-expulsing, second mode to said unstressed, first mode before the air pressure in said drip chamber drops to atmospheric pressure, thereby preventing an influx of air into said pathway through said bypass valve means.

3. A bypass valve assembly for use in a medical fluid administration set having a fluid pathway, a compressible drip chamber in the pathway, volume limiting means in the pathway including a membrane valve upstream of the drip chamber preventing air from passing downstream of the volume limiting means through the membrane valve in the pathway, the bypass valve assembly comprising:
air-venting bypass valve means mounted in the pathway intermediate the membrane valve and the drip chamber;
said bypass valve means operable in an unstressed, first mode wherein the pathway is closed at said bypass valve means to the atmosphere external to the pathway, and an air-expulsing, second mode upon compression of the drip chamber, wherein said bypass valve means permits air in the drip chamber to exit the administration set through said bypass valve means;
said bypass valve means gradually returning to said unstressed, first mode in response to the decreasing pressure of the exiting air, said bypass valve means relieving pressure exerted against the membrane valve by the air entrapped in the drip chamber during the compression thereof, said bypass valve means returning to said first mode before the air pressure in the drip chamber drops to the level of atmospheric pressure, thereby preventing an influx of air into the pathway through said bypass valve means from the pathway-external atmosphere.

4. A bypass valve assembly for use in a medical fluid administration set having a fluid pathway, a compressible drip chamber in the pathway, volume limiting means in the pathway including a membrane valve upstream of the drip chamber preventing air from passing downstream of the volume limiting means through the membrane valve in the pathway, the bypass valve assembly comprising:
an assembly housing forming part of the pathway and mounted intermediate the membrane valve and the drip chamber, said assembly housing defining a housing chamber;
air venting bypass valve means mounted in the assembly housing;
said bypass valve means operable in an unstressed, first mode wherein said bypass valve means is in sealing engagement with said assembly housing to close a defined assembly housing opening such that the pathway is closed at said bypass valve means to the atmosphere external to the pathway, and operable in an air-expulsing, second mode upon the air pressure within the housing chamber rising to a predetermined level such that said bypass valve means temporarily disengages from its seal with said assembly housing and provides for open communication between said housing chamber and the pathway-external atmosphere, such that air in said assembly housing exits the pathway through said defined assembly housing opening, said bypass valve means returning from said second mode to said first mode before the air pressure in said housing chamber drops to the level of atmospheric pressure.

5. The bypass valve assembly as in claim 4 further comprising a bypass valve support external of said assembly housing about said defined assembly housing opening, said valve support having a ridge therein, said ridge further including both a ridge opening and a groove therethrough, wherein said bypass valve means is mounted through said ridge opening such that in said unstressed first mode said groove is closed by said bypass valve means and in said air-expulsing second mode said valve support defines a channel including said groove communicating between said assembly housing opening and the atmosphere.

6. The bypass valve assembly as in claims 3, 4 or 5, wherein said bypass valve means comprises an umbrella valve.

7. The bypass valve assembly as in claims 4 or 5, wherein said assembly housing is integral with the volume limiting means.

8. The bypass valve assembly as in claim 1 wherein said assembly housing further includes a drip chamber cap having a drop forming member therein downstream of said housing chamber.

* * * * *

UNITED STATES PATENT AND TRADEMARK OFFICE
CERTIFICATE OF CORRECTION

PATENT NO. : 4,413,990
DATED : November 8, 1983
INVENTOR(S) : Herbert Mittleman

It is certified that error appears in the above-identified patent and that said Letters Patent are hereby corrected as shown below:

The first line of Claim 8 should read:

"8. The bypass valve assembly as in Claim 7 wherein"

Signed and Sealed this

Thirty-first Day of January 1984

[SEAL]

Attest:

GERALD J. MOSSINGHOFF

Attesting Officer          Commissioner of Patents and Trademarks